(12) United States Patent
Reiter

(10) Patent No.: US 10,282,878 B2
(45) Date of Patent: *May 7, 2019

(54) METHOD AND APPARATUS FOR ANNOTATING A GRAPHICAL OUTPUT

(71) Applicant: ARRIA DATA2TEXT LIMITED, Aberdeen (GB)

(72) Inventor: Ehud Baruch Reiter, Aberdeen (GB)

(73) Assignee: ARRIA DATA2TEXT LIMITED, Aberdeen (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,423

(22) Filed: Jun. 21, 2016

(65) Prior Publication Data

US 2017/0018107 A1 Jan. 19, 2017

Related U.S. Application Data

(63) Continuation of application No. 14/634,035, filed on Feb. 27, 2015, now Pat. No. 9,405,448, which is a
(Continued)

(51) Int. Cl.
*G06F 3/00* (2006.01)
*G06T 11/60* (2006.01)
(Continued)

(52) U.S. Cl.
CPC .......... *G06T 11/60* (2013.01); *G06F 3/04842* (2013.01); *G06F 17/2229* (2013.01);
(Continued)

(58) Field of Classification Search
CPC .. G06F 17/241; G06F 3/04842; G06F 17/229; G06F 17/248; G06F 17/2881; G06T 11/60; G06T 11/206; G06H 15/00
See application file for complete search history.

(56) References Cited

U.S. PATENT DOCUMENTS 5,181,250 A  1/1993  Morgan et al.
5,237,502 A  8/1993  White et al.
(Continued)

FOREIGN PATENT DOCUMENTS

AU  2011247830 B2  12/2011
AU  2011253627 B2  12/2011
(Continued)

OTHER PUBLICATIONS

Alawneh, A. L. et al., *Pattern Recognition Techniques Applied to the Abstraction of Traces of Inter-Process Communication*, Software Maintenance and Reengineering (CSMR), 2011 15th European Conference on Year: 2011, IEEE Conference Publications (2011) pp. 211-220.

(Continued)

*Primary Examiner* — Kyle R Stork
(74) *Attorney, Agent, or Firm* — Alston & Bird LLP

(57) ABSTRACT

Various methods are provided for generating and annotating a graph. One example method may include determining one or more key patterns in a primary data channel, wherein the primary data channel is derived from raw input data in response to a constraint being satisfied. A method may further include determining one or more significant patterns in one or more related data channels. A method may further include generating a natural language annotation for at least one of the one or more key patterns or the one or more significant patterns. A method may further include generating a graph that is configured to be displayed in a user interface, the graph having at least a portion of the one or more key patterns, the one or more significant patterns and the natural language annotation.

20 Claims, 6 Drawing Sheets

Related U.S. Application Data continuation of application No. PCT/US2012/053128, filed on Aug. 30, 2012.

(51) Int. Cl.
  *G06F 3/0484* (2013.01)
  *G06F 17/22* (2006.01)
  *G06F 17/24* (2006.01)
  *G06F 17/28* (2006.01)
  *G06T 11/20* (2006.01)
  *G16H 15/00* (2018.01)

(52) U.S. Cl.
  CPC .......... *G06F 17/241* (2013.01); *G06F 17/248* (2013.01); *G06F 17/2881* (2013.01); *G06T 11/206* (2013.01); *G16H 15/00* (2018.01)

(56) References Cited

U.S. PATENT DOCUMENTS

| | | |
|---|---|---|
| 5,311,429 A | 5/1994 | Tominaga |
| 5,321,608 A | 6/1994 | Namba et al. |
| 5,629,687 A | 5/1997 | Sutton et al. |
| 5,794,177 A | 8/1998 | Carus et al. |
| 5,802,488 A | 9/1998 | Edatsune |
| 6,023,669 A | 2/2000 | Suda et al. |
| 6,078,914 A | 6/2000 | Redfern |
| 6,138,087 A | 10/2000 | Budzinski |
| 6,266,617 B1 | 7/2001 | Evans |
| 6,442,485 B2 | 8/2002 | Evans |
| 6,466,899 B1 | 10/2002 | Yano et al. |
| 6,665,640 B1 | 12/2003 | Bennett et al. |
| 6,717,513 B1 | 4/2004 | Sandelman et al. |
| 6,947,885 B2 | 9/2005 | Bangalore et al. |
| 7,043,420 B2 | 5/2006 | Ratnaparkhi |
| 7,167,824 B2 | 1/2007 | Kallulli |
| 7,231,341 B2 | 6/2007 | Bangalore et al. |
| 7,238,313 B2 | 7/2007 | Ferencz et al. |
| 7,305,336 B2 | 12/2007 | Polanyi et al. |
| 7,310,969 B2 | 12/2007 | Dale |
| 7,346,493 B2 | 3/2008 | Ringger et al. |
| 7,418,447 B2 | 8/2008 | Caldwell et al. |
| 7,424,363 B2 | 9/2008 | Cheng et al. |
| 7,444,287 B2 | 10/2008 | Claudatos et al. |
| 7,496,621 B2 | 2/2009 | Pan et al. |
| 7,526,424 B2 | 4/2009 | Corston-Oliver et al. |
| 7,533,089 B2 | 5/2009 | Pan et al. |
| 7,562,005 B1 | 7/2009 | Bangalore et al. |
| 7,684,991 B2 | 3/2010 | Stohr et al. |
| 7,711,581 B2 | 5/2010 | Hood et al. |
| 7,783,486 B2 | 8/2010 | Rosser et al. |
| 7,809,552 B2 | 10/2010 | Pan et al. |
| 7,849,048 B2 | 12/2010 | Langseth et al. |
| 7,849,049 B2 | 12/2010 | Langseth et al. |
| 7,856,390 B2 | 12/2010 | Schiller |
| 7,873,509 B1 | 1/2011 | Budzinski |
| 7,921,091 B2 | 4/2011 | Cox et al. |
| 7,930,169 B2 | 4/2011 | Billerey-Mosier |
| 7,933,774 B1 | 4/2011 | Begeja et al. |
| 7,966,172 B2 | 6/2011 | Ruiz et al. |
| 7,970,601 B2 | 6/2011 | Burmester et al. |
| 7,979,267 B2 | 7/2011 | Ruiz et al. |
| 8,019,610 B2 | 9/2011 | Walker et al. |
| 8,024,331 B2 | 9/2011 | Calistri-Yeh et al. |
| 8,037,000 B2 | 10/2011 | Delmonico et al. |
| 8,082,144 B1 | 12/2011 | Brown et al. |
| 8,090,727 B2 | 1/2012 | Lachtarnik et al. |
| 8,150,676 B1 | 4/2012 | Kaeser |
| 8,175,873 B2 | 5/2012 | Di Fabbrizio et al. |
| 8,180,647 B2 | 5/2012 | Walker et al. |
| 8,180,758 B1 | 5/2012 | Cornali |
| 8,229,937 B2 | 7/2012 | Kiefer et al. |
| 8,355,903 B1 | 1/2013 | Birnbaum et al. |
| 8,374,848 B1 | 2/2013 | Birnbaum et al. |
| 8,425,325 B2 | 4/2013 | Hope |
| 8,473,911 B1 | 6/2013 | Baxter |
| 8,494,944 B2 | 7/2013 | Schiller |
| 8,515,733 B2 | 8/2013 | Jansen |
| 8,515,737 B2 | 8/2013 | Allen |
| 8,548,814 B2 | 10/2013 | Manuel-Devadoss |
| 8,548,915 B2 | 10/2013 | Antebi et al. |
| 8,561,014 B2 | 10/2013 | Mengusoglu et al. |
| 8,566,090 B2 | 10/2013 | Di Fabbrizio et al. |
| 8,589,148 B2 | 11/2013 | Atallah et al. |
| 8,589,172 B2 | 11/2013 | Alonso et al. |
| 8,616,896 B2 | 12/2013 | Lennox |
| 8,620,669 B2 | 12/2013 | Walker et al. |
| 8,626,613 B2 | 1/2014 | Dale et al. |
| 8,630,844 B1 | 1/2014 | Nichols et al. |
| 8,655,889 B2 | 2/2014 | Hua et al. |
| 8,676,691 B2 | 3/2014 | Schiller |
| 8,688,434 B1 | 4/2014 | Birnbaum et al. |
| 8,700,396 B1 | 4/2014 | Mengibar et al. |
| 8,738,384 B1 | 5/2014 | Bansal et al. |
| 8,738,558 B2 | 5/2014 | Antebi et al. |
| 8,762,134 B2 | 5/2014 | Reiter |
| 8,762,133 B2 | 6/2014 | Reiter |
| 8,775,161 B1 | 7/2014 | Nichols et al. |
| 8,825,533 B2 | 9/2014 | Basson et al. |
| 8,843,363 B2 | 9/2014 | Birnbaum et al. |
| 8,849,670 B2 | 9/2014 | Di Cristo et al. |
| 8,886,520 B1 | 11/2014 | Nichols et al. |
| 8,892,417 B1 | 11/2014 | Nichols et al. |
| 8,892,419 B2 | 11/2014 | Lundberg et al. |
| 8,898,063 B1 | 11/2014 | Sykes et al. |
| 8,903,711 B2 | 12/2014 | Lundberg et al. |
| 8,903,718 B2 | 12/2014 | Akuwudike |
| 8,909,595 B2 | 12/2014 | Gandy et al. |
| 8,914,452 B2 | 12/2014 | Boston et al. |
| 8,924,330 B2 | 12/2014 | Antebi et al. |
| 8,930,305 B2 | 1/2015 | Namburu et al. |
| 8,977,953 B1 | 3/2015 | Pierre et al. |
| 8,984,051 B2 | 3/2015 | Olsen et al. |
| 9,002,695 B2 | 4/2015 | Watanabe et al. |
| 9,002,869 B2 | 4/2015 | Riezler et al. |
| 9,015,730 B1 | 4/2015 | Allen et al. |
| 9,028,260 B2 | 5/2015 | Nanjiani et al. |
| 9,092,276 B2 | 7/2015 | Allen et al. |
| 9,104,720 B2 | 8/2015 | Rakshit et al. |
| 9,110,882 B2 | 8/2015 | Overell et al. |
| 9,110,977 B1 | 8/2015 | Pierre et al. |
| 9,111,534 B1 | 8/2015 | Sylvester et al. |
| 9,135,244 B2 | 9/2015 | Reiter |
| 9,135,662 B2 | 9/2015 | Evenhouse et al. |
| 9,146,904 B2 | 9/2015 | Allen |
| 9,164,982 B1 | 10/2015 | Kaeser |
| 9,190,054 B1 | 11/2015 | Riley et al. |
| 9,208,147 B1 | 12/2015 | Nichols et al. |
| 9,229,927 B2 | 1/2016 | Wolfram et al. |
| 9,240,197 B2 | 1/2016 | Begeja et al. |
| 9,244,894 B1 | 1/2016 | Dale et al. |
| 9,251,134 B2 | 2/2016 | Birnbaum et al. |
| 9,251,143 B2 | 2/2016 | Bird et al. |
| 9,263,039 B2 | 2/2016 | Di Cristo et al. |
| 9,268,770 B1 | 2/2016 | Kursun |
| 9,323,743 B2 | 4/2016 | Reiter |
| 9,405,448 B2 | 8/2016 | Reiter |
| 9,640,045 B2 | 5/2017 | Reiter |
| 10,026,274 B2 | 7/2018 | Reiter |
| 2002/0026306 A1 | 2/2002 | Bangalore et al. |
| 2003/0131315 A1* | 7/2003 | Escher .................. G06N 3/126 715/255 |
| 2003/0212545 A1 | 11/2003 | Kallulli |
| 2004/0246120 A1 | 12/2004 | Benner et al. |
| 2005/0039107 A1 | 2/2005 | Hander et al. |
| 2005/0228635 A1 | 10/2005 | Araki et al. |
| 2005/0256703 A1 | 11/2005 | Markel |
| 2006/0085667 A1* | 4/2006 | Kubota ............. G06F 17/30719 714/4.1 |
| 2006/0178868 A1 | 8/2006 | Billerey-Mosier |
| 2006/0259293 A1 | 11/2006 | Orwant |
| 2007/0078655 A1 | 4/2007 | Semkow et al. |
| 2007/0106628 A1 | 5/2007 | Adjali et al. |
| 2007/0129942 A1 | 6/2007 | Ban et al. |

(56) References Cited

U.S. PATENT DOCUMENTS

| | | |
|---|---|---|
| 2007/0143099 A1 | 6/2007 | Balchandran et al. |
| 2008/0221865 A1 | 9/2008 | Wellmann |
| 2008/0221870 A1 | 9/2008 | Attardi et al. |
| 2008/0281781 A1 | 11/2008 | Zhao et al. |
| 2008/0312954 A1 | 12/2008 | Ullrich et al. |
| 2009/0089100 A1 | 4/2009 | Nenov et al. |
| 2009/0089126 A1 | 4/2009 | Odubiyi |
| 2009/0111486 A1 | 4/2009 | Burstrom |
| 2009/0156229 A1 | 6/2009 | Hein et al. |
| 2009/0198496 A1 | 8/2009 | Denecke |
| 2009/0281839 A1 | 11/2009 | Lynn et al. |
| 2009/0286514 A1 | 11/2009 | Lichorowic et al. |
| 2009/0287567 A1* | 11/2009 | Penberthy .............. G06F 17/30 705/14.43 |
| 2010/0146491 A1 | 6/2010 | Hirano et al. |
| 2010/0153095 A1 | 6/2010 | Yang et al. |
| 2010/0174545 A1 | 7/2010 | Otani |
| 2010/0191658 A1 | 7/2010 | Kannan et al. |
| 2010/0203970 A1 | 8/2010 | Hope |
| 2010/0332235 A1 | 12/2010 | David |
| 2011/0010164 A1 | 1/2011 | Williams |
| 2011/0068929 A1 | 3/2011 | Franz et al. |
| 2011/0087486 A1 | 4/2011 | Schiller |
| 2011/0160986 A1 | 6/2011 | Wu et al. |
| 2011/0179006 A1 | 7/2011 | Cox et al. |
| 2011/0218822 A1 | 9/2011 | Buisman et al. |
| 2011/0225185 A1 | 9/2011 | Gupta |
| 2011/0257839 A1 | 10/2011 | Mukherjee |
| 2012/0078888 A1 | 3/2012 | Brown et al. |
| 2012/0084027 A1 | 4/2012 | Caine |
| 2012/0136649 A1 | 5/2012 | Freising et al. |
| 2012/0158089 A1 | 6/2012 | Bocek et al. |
| 2012/0173475 A1 | 7/2012 | Ash et al. |
| 2012/0290289 A1 | 11/2012 | Manera et al. |
| 2012/0310990 A1 | 12/2012 | Viegas et al. |
| 2013/0030810 A1 | 1/2013 | Kopparapu et al. |
| 2013/0066873 A1 | 3/2013 | Salvetti et al. |
| 2013/0144606 A1 | 6/2013 | Birnbaum et al. |
| 2013/0145242 A1 | 6/2013 | Birnbaum et al. |
| 2013/0151238 A1 | 6/2013 | Beaurpere et al. |
| 2013/0174026 A1 | 7/2013 | Locke |
| 2013/0185050 A1 | 7/2013 | Bird et al. |
| 2013/0211855 A1 | 8/2013 | Eberle et al. |
| 2013/0238329 A1 | 9/2013 | Casella dos Santos |
| 2013/0238330 A1 | 9/2013 | Casella dos Santos |
| 2013/0238987 A1 | 9/2013 | Lutwyche |
| 2013/0251233 A1 | 9/2013 | Yang et al. |
| 2013/0268263 A1 | 10/2013 | Park et al. |
| 2013/0293363 A1 | 11/2013 | Plymouth et al. |
| 2013/0311201 A1 | 11/2013 | Chatfield et al. |
| 2014/0019531 A1 | 1/2014 | Czajka et al. |
| 2014/0025371 A1 | 1/2014 | Min |
| 2014/0039878 A1 | 2/2014 | Wasson |
| 2014/0052696 A1* | 2/2014 | Soroushian ........ H04N 21/4665 707/691 |
| 2014/0062712 A1 | 3/2014 | Reiter |
| 2014/0067377 A1 | 3/2014 | Reiter |
| 2014/0072947 A1 | 3/2014 | Boguraev et al. |
| 2014/0072948 A1 | 3/2014 | Boguraev et al. |
| 2014/0089915 A1 | 3/2014 | Sbodio |
| 2014/0100846 A1 | 4/2014 | Haine et al. |
| 2014/0100901 A1 | 4/2014 | Haine et al. |
| 2014/0100923 A1 | 4/2014 | Strezo et al. |
| 2014/0143720 A1 | 5/2014 | Dimarco et al. |
| 2014/0149107 A1 | 5/2014 | Schilder |
| 2014/0164303 A1 | 6/2014 | Bagchi et al. |
| 2014/0164304 A1 | 6/2014 | Bagchi et al. |
| 2014/0188477 A1 | 7/2014 | Zhang |
| 2014/0278358 A1 | 9/2014 | Byron et al. |
| 2014/0281935 A1 | 9/2014 | Byron et al. |
| 2014/0281951 A1 | 9/2014 | Megiddo et al. |
| 2014/0297268 A1 | 10/2014 | Govrin et al. |
| 2014/0316768 A1 | 10/2014 | Khandekar |
| 2014/0375466 A1 | 12/2014 | Reiter |
| 2014/0379322 A1 | 12/2014 | Koutrika et al. |
| 2014/0379378 A1 | 12/2014 | Cohen-Solal et al. |
| 2015/0006437 A1 | 1/2015 | Byron et al. |
| 2015/0032443 A1 | 1/2015 | Karov et al. |
| 2015/0081307 A1 | 3/2015 | Cederstrom et al. |
| 2015/0081321 A1 | 3/2015 | Jain |
| 2015/0095015 A1 | 4/2015 | Lani et al. |
| 2015/0106307 A1 | 4/2015 | Antebi et al. |
| 2015/0142418 A1 | 5/2015 | Byron et al. |
| 2015/0142421 A1 | 5/2015 | Buurman et al. |
| 2015/0154359 A1 | 6/2015 | Harris et al. |
| 2015/0163358 A1 | 6/2015 | Klemm et al. |
| 2015/0169522 A1 | 6/2015 | Logan et al. |
| 2015/0169548 A1 | 6/2015 | Reiter |
| 2015/0169659 A1 | 6/2015 | Lee et al. |
| 2015/0169720 A1 | 6/2015 | Byron et al. |
| 2015/0169737 A1 | 6/2015 | Bryon et al. |
| 2015/0179082 A1 | 6/2015 | Byron et al. |
| 2015/0227508 A1 | 8/2015 | Howald et al. |
| 2015/0242384 A1 | 8/2015 | Reiter |
| 2015/0261744 A1 | 9/2015 | Suenbuel et al. |
| 2015/0261836 A1 | 9/2015 | Madhani et al. |
| 2015/0279348 A1 | 10/2015 | Cao et al. |
| 2015/0310013 A1 | 10/2015 | Allen et al. |
| 2015/0310112 A1 | 10/2015 | Allen et al. |
| 2015/0310861 A1 | 10/2015 | Waltermann et al. |
| 2015/0324343 A1 | 11/2015 | Carter et al. |
| 2015/0324347 A1 | 11/2015 | Bradshaw et al. |
| 2015/0324351 A1 | 11/2015 | Sripada et al. |
| 2015/0324374 A1 | 11/2015 | Sripada et al. |
| 2015/0324413 A1 | 11/2015 | Gubin et al. |
| 2015/0325000 A1 | 11/2015 | Sripada |
| 2015/0326622 A1 | 11/2015 | Carter et al. |
| 2015/0331845 A1 | 11/2015 | Guggilla et al. |
| 2015/0331846 A1 | 11/2015 | Guggilla et al. |
| 2015/0332670 A1 | 11/2015 | Akbacak et al. |
| 2015/0347400 A1 | 12/2015 | Sripada |
| 2015/0356127 A1 | 12/2015 | Pierre et al. |
| 2015/0363363 A1 | 12/2015 | Bohra et al. |
| 2015/0363364 A1 | 12/2015 | Sripada |
| 2015/0363382 A1 | 12/2015 | Bohra et al. |
| 2015/0363390 A1 | 12/2015 | Mungi et al. |
| 2015/0363391 A1 | 12/2015 | Mungi et al. |
| 2015/0371651 A1 | 12/2015 | Aharoni et al. |
| 2016/0019200 A1 | 1/2016 | Allen |
| 2016/0027125 A1 | 1/2016 | Bryce |
| 2016/0055150 A1 | 2/2016 | Bird et al. |
| 2016/0132489 A1 | 5/2016 | Reiter |
| 2016/0140090 A1 | 5/2016 | Dale et al. |
| 2016/0328385 A1 | 11/2016 | Reiter |

FOREIGN PATENT DOCUMENTS

| | | |
|---|---|---|
| AU | 2013201755 A1 | 9/2013 |
| AU | 2013338351 A1 | 5/2015 |
| CA | 2577721 C | 3/2006 |
| CA | 2826116 C | 3/2006 |
| CN | 103999081 A | 8/2014 |
| CN | 104182059 A | 12/2014 |
| CN | 104881320 A | 9/2015 |
| EP | 1366955 B1 | 5/2006 |
| EP | 2707809 A1 | 3/2014 |
| EP | 2750759 A1 | 7/2014 |
| EP | 2849103 A2 | 3/2015 |
| GB | 2518192 A | 3/2015 |
| JP | 61-221873 A | 10/1986 |
| JP | 2004-21791 A | 1/2004 |
| JP | 2014165766 A | 9/2014 |
| WO | WO 2009/014465 A2 | 1/2000 |
| WO | WO 2000/074394 A2 | 12/2000 |
| WO | WO 2002/031628 A2 | 4/2002 |
| WO | WO 2002/073449 A1 | 9/2002 |
| WO | WO 2002/073531 A1 | 9/2002 |
| WO | WO 2002/031628 A3 | 10/2002 |
| WO | WO 2006/010044 A2 | 1/2006 |
| WO | WO 2007/041221 A1 | 4/2007 |
| WO | WO 2010/049925 A2 | 5/2010 |
| WO | WO 2010/051404 A1 | 5/2010 |
| WO | WO 2012/071571 A2 | 5/2012 |
| WO | WO 2013/009613 A1 | 1/2013 |

(56) References Cited

FOREIGN PATENT DOCUMENTS

| WO | WO 2013/042115 A2 | 3/2013 |
| --- | --- | --- |
| WO | WO 2013/042116 A1 | 3/2013 |
| WO | WO 2013/177280 A1 | 11/2013 |
| WO | WO 2014/035402 A1 | 3/2014 |
| WO | WO 2014/098560 A2 | 6/2014 |
| WO | WO 2014/140977 A1 | 9/2014 |
| WO | WO 2014/187076 A1 | 11/2014 |
| WO | WO 2015/028844 A1 | 3/2015 |
| WO | WO 2015/113301 A1 | 8/2015 |
| WO | WO 2015/148278 A1 | 10/2015 |
| WO | WO 2015/159133 A1 | 10/2015 |
| WO | WO 2015/164253 A1 | 10/2015 |
| WO | WO 2015/175338 A1 | 11/2015 |
| WO | WO 2016/004266 A2 | 1/2016 |

OTHER PUBLICATIONS

Andre, E. et al., *From Visual Data to Multimedia Presentations*, Grounding Representations: Integration of Sensory Information in Natural Language Processing, Artificial Intelligence and Neural networks, IEE Colloquium on (May 15, 1995) pp. 1-3.

Andre, E. et al., *Natural Language Access to Visual Data: Dealing with Space and Movement*, Report 63, German Research Center for Artificial Intelligence (DFKI) SFB 314, Project VITRA, (Nov. 1989) 1-21.

Barzilay, R., et al.; "*Aggregation via Set Partitioning for Natural Language Generation*;" Proceedings of the Human Language Technology Conference of the North American Chapter of the ACL; pp. 359-366; dated Jun. 2006.

Bhoedjang, R. A. F. et al., *Optimizing Distributed Data Structures Using Application-Specific Network Interface Software*, Parallel Processing, 1998, Proceedings; 1998 International Conference on Year: 1998, IEEE Conference Publications (1998) pp. 485-492.

Cappozzo, A. et al., *Surface-Marker Cluster Design Criteria for 3-D Bone Movement Reconstruction*, IEEE Transactions on Biomedical Engineering, vol. 44, No. 12 (Dec. 1997) 1165-1174.

Dalianis, H. et al.; "*Aggregation in Natural Language Generation*;" Trends in Natural Language Generation, an Artificial Intelligence Perspective; pp. 88-105; dated 1996.

Dragon, R. et al., *Multi-Scale Clustering of Frame-to-Frame Correspondences for Motion Segmentation*, Computer Vision ECCV 2012, Springer Berlin Heidelberg (Oct. 7, 2012) 445-458.

Gatt, A. et al., *From Data to Text in the Neonatal Intensive Care Unit: Using NLG Technology for Decision Support and Information Management*, AI Communication (Jan. 1, 2009) 153-186.

Gorelov, S. s. et al., *Search Optimization in Semistructured Databases Using Hierarchy of Document Schemas*, Programming and Computer Software, vol. 31, No. 6 (2005) 321-331.

Herzog, G. et al., *Combining Alternatives in the Multimedia Presentation of Decision Support Information for Real-Time Control*, IFIP (1998) 15 pages.

International Preliminary Report on Patentability for Application No. PCT/IB2012/056513 dated May 19, 2015.

International Preliminary Report on Patentability for Application No. PCT/IB2012/056514 dated May 19, 2015.

International Preliminary Report on Patentability for Application No. PCT/IB2012/057773 dated Jun. 30, 2015.

International Preliminary Report on Patentability for Application No. PCT/IB2012/057774 dated Jun. 30, 2015.

International Preliminary Report on Patentability for Application No. PCT/IB2013/050375 dated Jul. 21, 2015.

International Preliminary Report on Patentability for Application No. PCT/IB2013/058131 dated May 5, 2015.

International Preliminary Report on Patentability for Application No. PCT/IB2014/060846 dated Oct. 18, 2016.

International Preliminary Report on Patentability for Application No. PCT/US2012/053115 dated Mar. 3, 2015.

International Preliminary Report on Patentability for Application No. PCT/US2012/053127 dated Mar. 3, 2015.

International Preliminary Report on Patentability for Application No. PCT/US2012/053128 dated Mar. 3, 2015.

International Preliminary Report on Patentability for Application No. PCT/US2012/053156 dated Mar. 3, 2015.

International Preliminary Report on Patentability for Application No. PCT/US2012/053183 dated Mar. 3, 2015.

International Preliminary Report on Patentability for Application No. PCT/US2012/061051 dated Mar. 3, 2015.

International Preliminary Report on Patentability for Application No. PCT/US2012/063343 dated May 5, 2015.

International Search Report and Written Opinion for Application No. PCT/IB2012/056513 dated Jun. 26, 2013.

International Search Report and Written Opinion for Application No. PCT/IB2012/056514 dated Jun. 26, 2013.

International Search Report and Written Opinion for Application No. PCT/IB2012/057773 dated Jul. 1, 2013.

International Search Report and Written Opinion for Application No. PCT/IB2012/057774 dated Sep. 20, 2013.

International Search Report and Written Opinion for Application No. PCT/IB2013/050375 dated May 7, 2013.

International Search Report and Written Opinion for Application No. PCT/IB2014/060846 dated Feb. 4, 2015.

International Search Report and Written Opinion for Application No. PCT/US2012/053115 dated Jul. 24, 2013.

International Search Report and Written Opinion for Application No. PCT/US2012/053127 dated Jul. 24, 2013.

International Search Report and Written Opinion for Application No. PCT/US2012/053128 dated Jun. 27, 2013.

International Search Report and Written Opinion for Application No. PCT/US2012/053156 dated Sep. 26, 2013.

International Search Report and Written Opinion for Application No. PCT/US2012/053183 dated Jun. 4, 2013.

International Search Report and Written Opinion for Application No. PCT/US2012/061051 dated Jul. 24, 2013.

International Search Report and Written Opinion for Application No. PCT/US2012/063343; dated Jan. 15, 2014.

International Search Report and Written Opinion for Application No. PCT/IB2013/058131 dated Jul. 3, 2014.

Kottke, D. P. et al., *Motion Estimation Via Cluster Matching*, 8180 IEEE Transactions on Pattern Analysis and Machine Intelligence 16, No. 11 (Nov. 1994) 1128-1132.

Kukich, K., *Knowledge-Based Report Generation: A Knowledge-Engineering Approach to Natural Language Report Generation*, Dissertation to The Interdisciplinary Department of Information Science, University of Pittsburg (Aug. 1983) 260 pages.

Leonov, A. v. et al., *Construction of an Optimal Relational Schema for Storing XML Documents in an RDBMS Without Using DTD/XML Schema*, Programming and Computer Software, vol. 30, No. 6 (2004) 323-336.

Notice of Allowance for U.S. Appl. No. 14/023,023 dated Apr. 11, 2014.

Notice of Allowance for U.S. Appl. No. 14/023,056 dated Apr. 29, 2014.

Notice of Allowance for U.S. Appl. No. 14/311,806 dated Dec. 28, 2016.

Notice of Allowance for U.S. Appl. No. 14/311,998 dated Dec. 22, 2015.

Notice of Allowance for U.S. Appl. No. 14/311,998 dated Jan. 21, 2016.

Notice of Allowance for U.S. Appl. No. 14/634,035 dated Mar. 30, 2016.

Office Action for U.S. Appl. No. 14/023,023 dated Mar. 4, 2014.
Office Action for U.S. Appl. No. 14/023,056 dated Nov. 21, 2013.
Office Action for U.S. Appl. No. 14/311,806 dated Jun. 10, 2016.
Office Action for U.S. Appl. No. 14/311,998 dated Feb. 20, 2015.
Office Action for U.S. Appl. No. 14/311,998 dated Oct. 7, 2015.
Office Action for U.S. Appl. No. 14/634,035 dated Aug. 28, 2015.
Office Action for U.S. Appl. No. 14/634,035 dated Dec. 10, 2015.
Office Action for U.S. Appl. No. 14/634,035 dated Mar. 30, 2016.
Office Action for U.S. Appl. No. 15/074,425 dated May 10, 2017.
Office Action for U.S. Appl. No. 15/421,921 dated Sep. 27, 2017.

(56) References Cited

OTHER PUBLICATIONS

Perry, B. et al., *Automatic Realignment of Data Structures to Improve MPI Performance*, Networks (ICN), 2010 Ninth International Conference on Year: 2010, IEEE Conference Publications (2010) pp. 42-47.
Quinlan, J. R., *Induction of Decision Trees*, Machine Learning, Kluwer Academic Publishers, vol. 1, No. 1 (Jan. 1, 1986) 81-106.
Radev, D. R. et al., *Generating Natural Language Summaries from Multiple On-Line Sources*, Association of Computational Linguistics, vol. 24, No. 3 (1998) 469-500.
Reiter, E. et al., *Building Applied Natural Language Generation Systems*, Natural Language Engineering 1 (1) (1995) 31 pages.
Reiter, E., *An Architecture for Data-to-Text Systems*, Proceedings of ENLG-2007 (Jun. 20, 2007) 97-104.
Reiter, E., et al.; "*Studies in Natural Language Processing—Building Natural Language Generation Systems*;" Cambridge University Press; dated 2000.
Shaw, J.; "*Clause Aggregation Using Linguistic Knowledge*;" Proceedings of IWNLG; pp. 138-147; dated Jan. 1998; retrieved from <http://acl.ldc.upenn.edu/W/W98/W98-1415.pdf>.
Spillner, J. et al., *Algorithms for Dispersed Processing*, Utility and Cloud Computing (UC), 204 IEEE/ACM 7th International Conference on Year: 2014, IEEE Conferenced Publications (2014) pp. 914-921.
Statement in accordance with the Notice from the European patent Office dated Oct. 1, 2007 concerning business methods (OJ EPO Nov. 2007, 592-593, (XP002456414) 1 page.
U.S. Appl. No. 13/186,308; entitled "Method and Apparatus for Triggering the Automatic Generation of Narratives" filed Jul. 19, 2011.
U.S. Appl. No. 13/186,329; entitled "Method and Apparatus for Triggering the Automatic Generation of Narratives".
U.S. Appl. No. 13/186,337; entitled "Method and Apparatus for Triggering the Automatic Generation of Narratives" filed Jul. 19, 2011.
U.S. Appl. No. 13/186,346; entitled "Method and Apparatus for Triggering the Automatic Generation of Narratives" filed Jul. 19, 2011.
U.S. Appl. No. 13/464,635; entitled "Use of Tools and Abstraction in a Configurable and Portable System for Generating Narratives" filed May 4, 2012.
U.S. Appl. No. 13/464,675; entitled "Configurable and Portable System for Generating Narratives" filed May 4, 2012.
U.S. Appl. No. 13/464,716; entitled "Configurable and Portable System for Generating Narratives" filed May 4, 2012.
U.S. Appl. No. 12/779,636; entitled "System and Method for Using Data to Automatically Generate a Narrative Story" filed May 13, 2010.
U.S. Appl. No. 14/023,023; entitled "Method and Apparatus for Alert Validation;" filed Sep. 10, 2013.
U.S. Appl. No. 14/023,056; entitled "Method and Apparatus for Situational Analysis Text Generation," filed Sep. 10, 2013.
U.S. Appl. No. 14/027,684; entitled "Method, Apparatus, and Computer Program Product for User-Directed Reporting;" filed Sep. 16, 2013.
U.S. Appl. No. 14/027,775; entitled "Method and Apparatus for Interactive Reports;" filed Sep. 16, 2013.
U.S. Appl. No. 14/311,998, entitled Method and Apparatus for Situational Analysis Text Generation; In re: Reiter; filed Jun. 23, 2014.
U.S. Appl. No. 14/634,035, entitled Method and Apparatus for Annotating a Graphical Output; In re: Reiter; filed Feb. 27, 2015.
U.S. Appl. No. 14/311,806; entitled Method and Apparatus for Alert Validation; In re: Reiter, filed Jun. 23, 2014.
U.S. Appl. No. 14/914,461, filed Feb. 25, 2016; In re: Reiter et al., entitled Text Generation From Correlated Alerts.
U.S. Appl. No. 15/022,420, filed Mar. 16, 2016; In re: Mahamood, entitled Method and Apparatus for Document Planning.
U.S. Appl. No. 15/074,425, filed Mar. 18, 2016; In re: Reiter, entitled Method and Apparatus for Situational Analysis Text Generation.
U.S. Appl. No. 15/093,337, filed Apr. 7, 2016; In re: Reiter, entitled Method and Apparatus for Referring Expression Generation.
U.S. Appl. No. 15/093,365, filed Apr. 7, 2016; In re: Logan et al., entitled Method and Apparatus for Updating a Previously Generated Text.
U.S. Appl. No. 15/421,921, filed Feb. 1, 2017; In re: Reiter, entitled Method and Apparatus for Alert Validation.
Voelz, D. et al., *Rocco: A RoboCup Soccer Commentator System*, German Research Center for Artificial Intelligence DFKI GmbH (1999) 11 pages.
Yu, J. et al., *Choosing the Content of Textual Summaries of Large Time-Series Data Sets*, Natural Language Engineering 13, (Jan. 1, 2007) pp. 1-28.
Notice of Allowance for U.S. Appl. No. 15/421,921 dated Mar. 14, 2018.
Office Action for U.S. Appl. No. 15/074,425 dated Feb. 26, 2018.

\* cited by examiner

METHOD AND APPARATUS FOR ANNOTATING A GRAPHICAL OUTPUT

CROSS-REFERENCE TO RELATED APPLICATIONS

This application is a continuation of U.S. application Ser. No. 14/634,035, filed Feb. 27, 2015, which is a continuation of International Application No. PCT/US2012/053128, filed Aug. 30, 2012, both of which are hereby incorporated herein in their entirety by reference.

TECHNOLOGICAL FIELD

Embodiments of the present invention relate generally to natural language generation technologies and, more particularly, relate to a method, apparatus, and computer program product for textually annotating a graphical output.

BACKGROUND

In some examples, a natural language generation (NLG) system is configured to transform raw input data that is expressed in a non-linguistic format into a format that can be expressed linguistically, such as through the use of natural language. For example, raw input data may take the form of a value of a stock market index over time and, as such, the raw input data may include data that is suggestive of a time, a duration, a value and/or the like. Therefore, an NLG system may be configured to input the raw input data and output text that linguistically describes the value of the stock market index. For example, "securities markets rose steadily through most of the morning, before sliding downhill late in the day."

Data that is input into a NLG system may be provided in, for example, a recurrent formal structure. The recurrent formal structure may comprise a plurality of individual fields and defined relationships between the plurality of individual fields. For example, the input data may be contained in a spreadsheet or database, presented in a tabulated log message or other defined structure, encoded in a 'knowledge representation' such as the resource description framework (RDF) triples that make up the Semantic Web and/or the like. In some examples, the data may include numerical content, symbolic content or the like. Symbolic content may include, but is not limited to, alphanumeric and other non-numeric character sequences in any character encoding, used to represent arbitrary elements of information. In some examples, the output of the NLG system is text in a natural language (e.g. English, Japanese or Swahili), but may also be in the form of synthesized speech.

BRIEF SUMMARY

Methods, apparatuses, and computer program products are described herein that are configured to generate a graph that is configured to display one or more key patterns that are detected in a data channel. In some example embodiments, the graph may also include one or more significant patterns in one or more related channels and/or events. In further examples, a time period or duration of the data shown in the graph may be selected such that the displayed graph illustrates the portion of the data channel that contains the one or more key patterns. The output graph is further configured to include textual annotations that provide a textual comment, phrase or otherwise is configured to explain, using text, the one or more key patterns, the one or more significant patterns and/or the events in a contextual channel in natural language. In further examples, the textual annotations are generated from the raw input data and further are designed, in some examples, to textually describe identified patterns, anomalies and/or the context of the graph. In some examples, a narrative may be included with the graph that provides situational awareness or an overview of the data/patterns displayed on and/or off of the graph. Advantageously, for example, the graph is configured to visually provide situational awareness to a viewer.

BRIEF DESCRIPTION OF THE DRAWINGS

Figure 1:
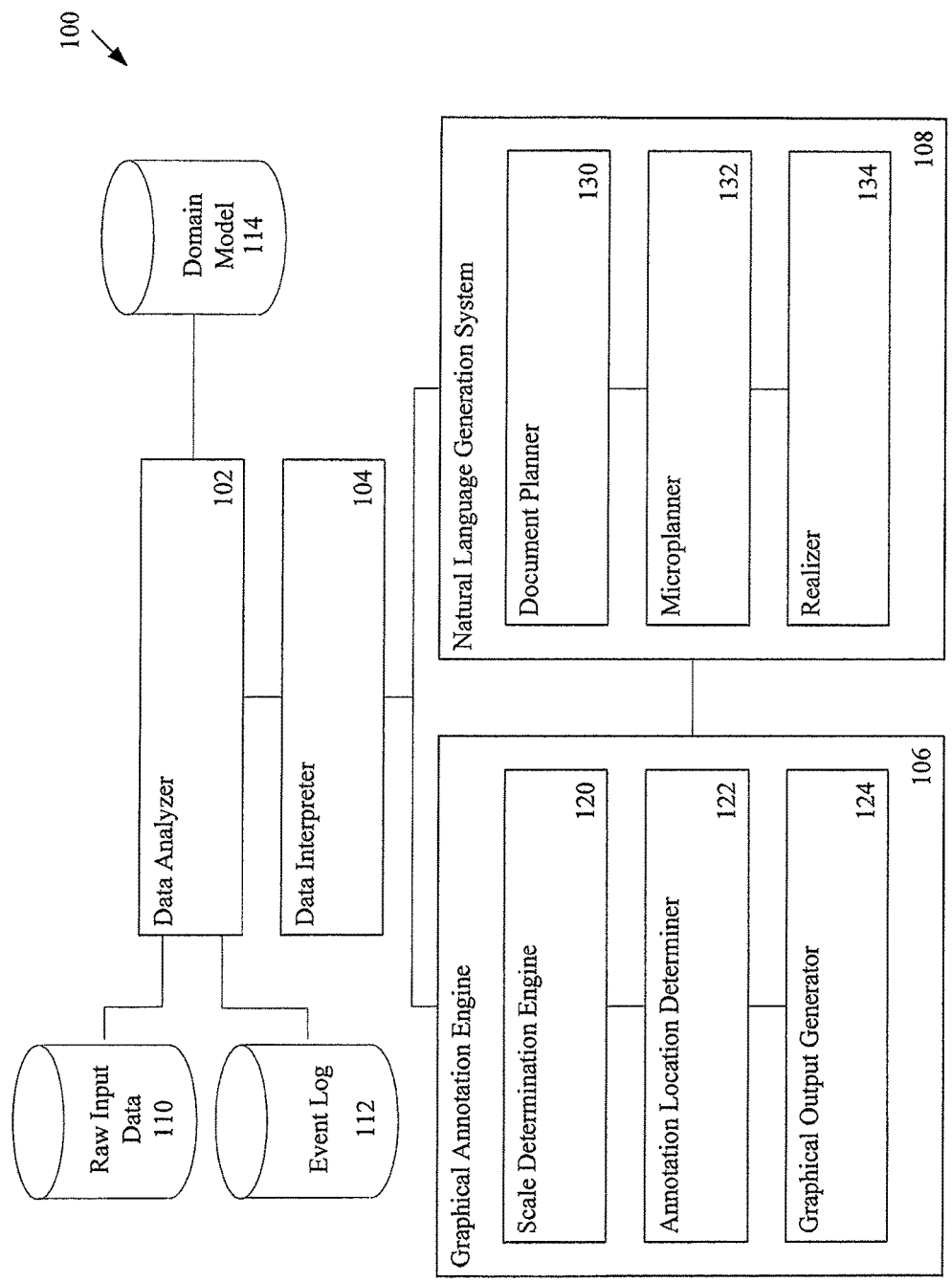
Figure 2:
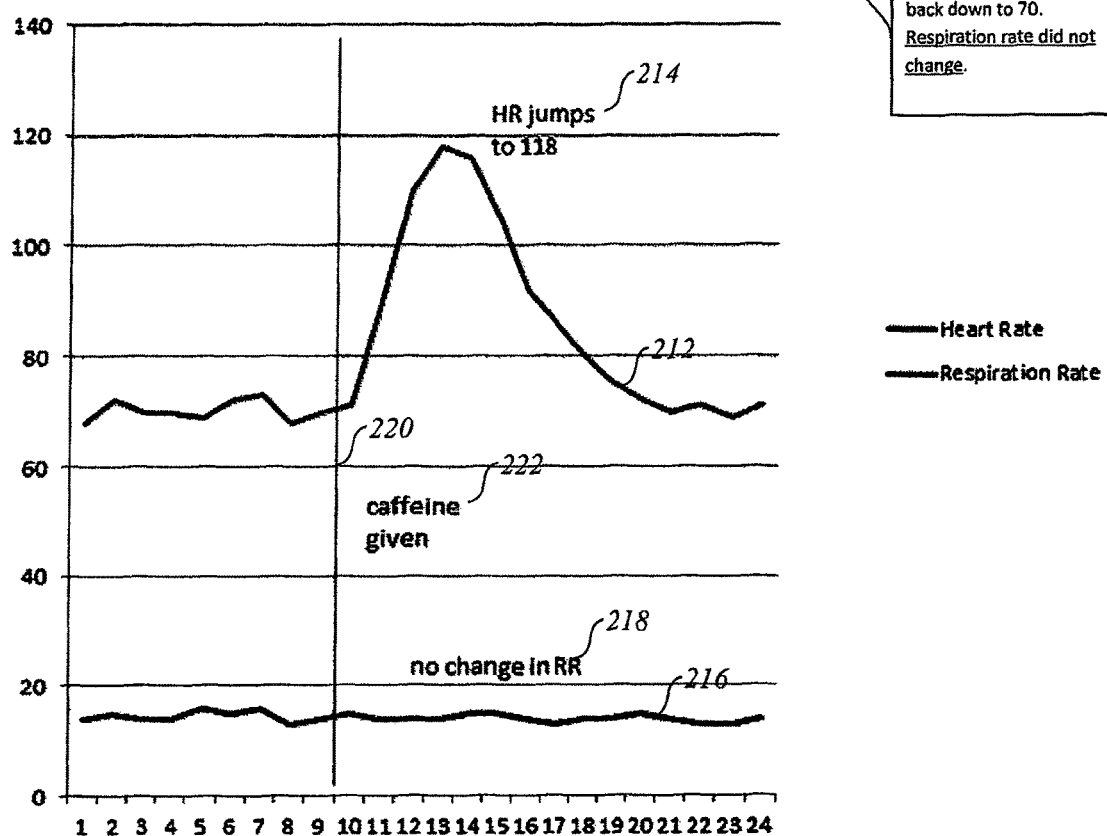
Figure 3:
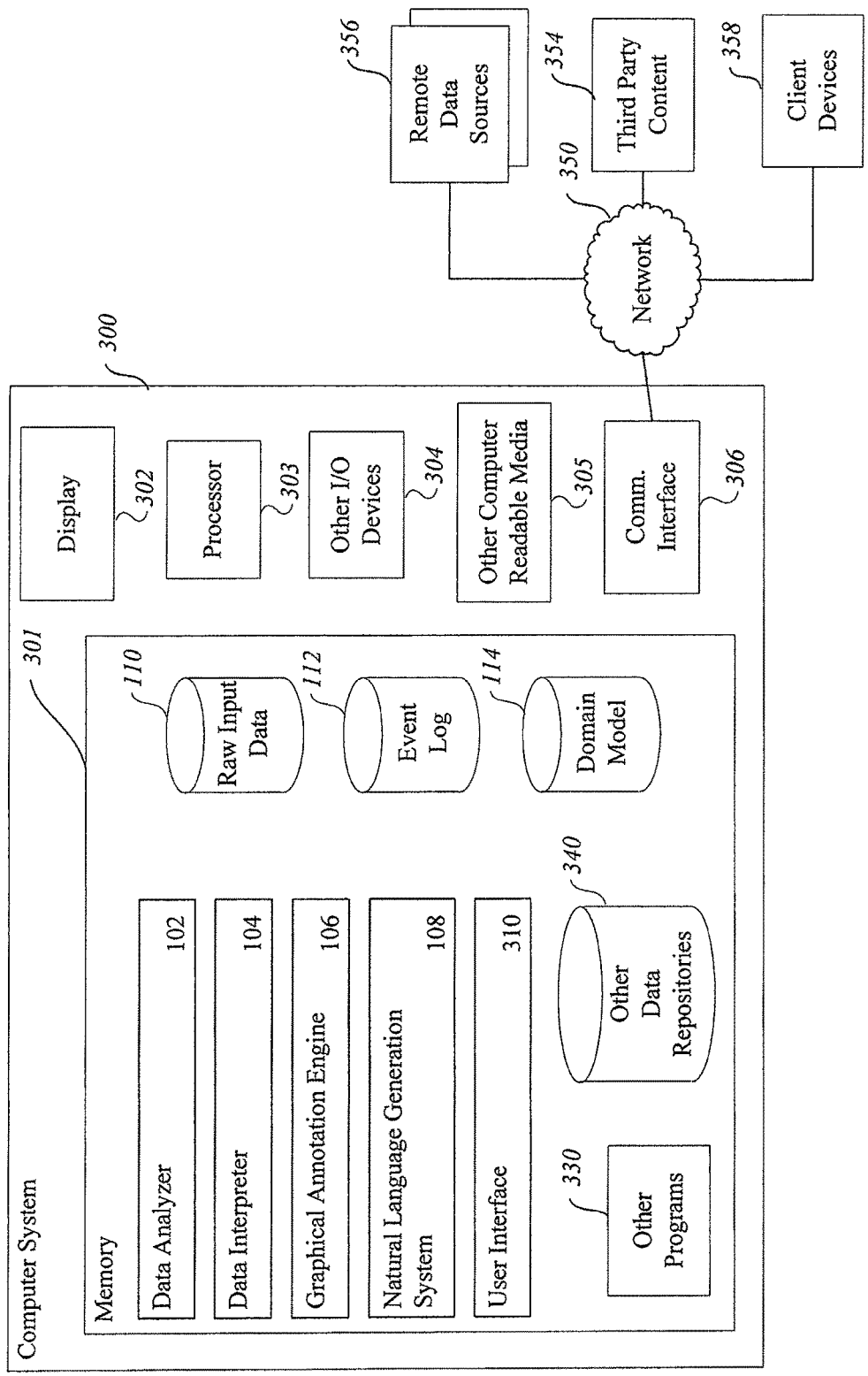
Figure 4:
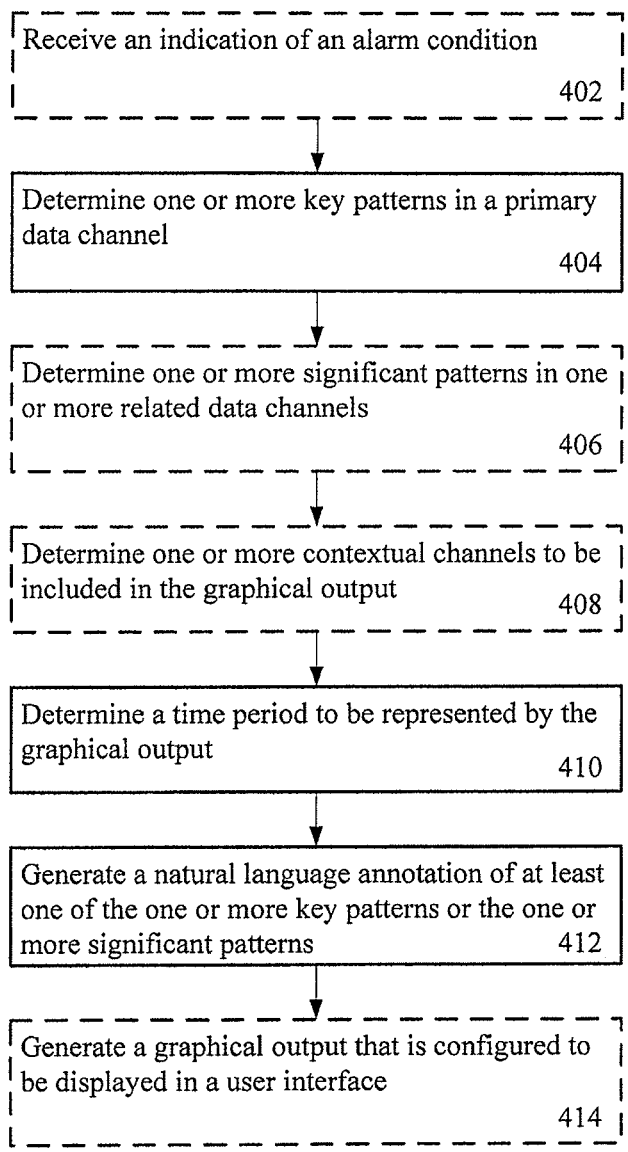
Figure 5:
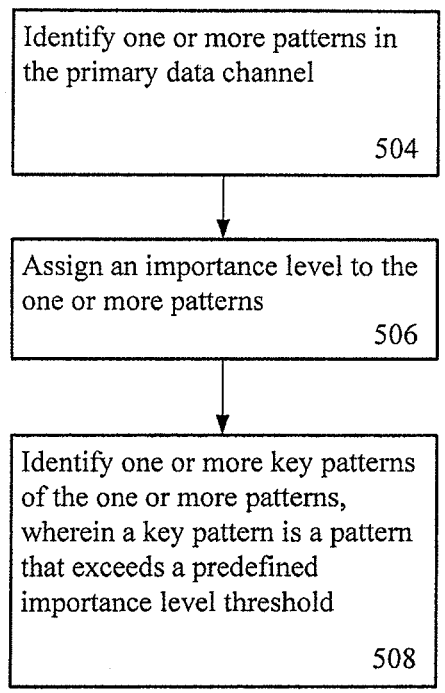
Figure 6:
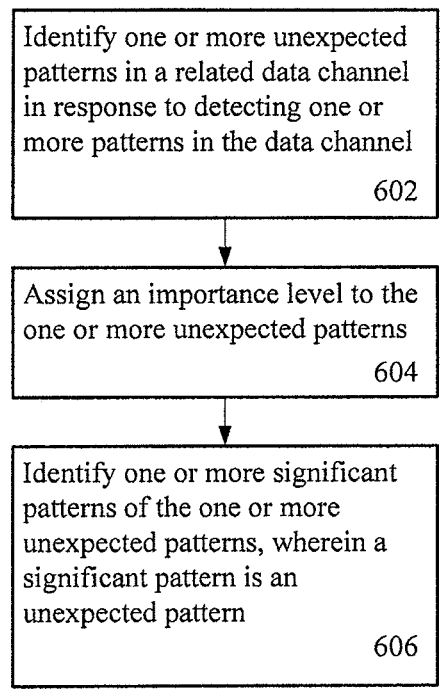

Having thus described embodiments of the invention in general terms, reference will now be made to the accompanying drawings, which are not necessarily drawn to scale, and wherein:

FIG. 1 is a schematic representation of a graphical annotation system that may benefit from some example embodiments of the present invention;

FIG. 2 illustrates an example graphical output in accordance with some example embodiments of the present invention;

FIG. 3 illustrates a block diagram of an apparatus that embodies a graphical annotation system in accordance with some example embodiments of the present invention; and FIGS. 4-6 illustrate flowcharts that may be performed by a graphical annotation system in accordance with some example embodiments of the present invention.

DETAILED DESCRIPTION

Example embodiments will now be described more fully hereinafter with reference to the accompanying drawings, in which some, but not all embodiments are shown. Indeed, the embodiments may take many different forms and should not be construed as limited to the embodiments set forth herein; rather, these embodiments are provided so that this disclosure will satisfy applicable legal requirements. Like reference numerals refer to like elements throughout. The terms "data," "content," "information," and similar terms may be used interchangeably, according to some example embodiments, to refer to data capable of being transmitted, received, operated on, and/or stored. Moreover, the term "exemplary", as may be used herein, is not provided to convey any qualitative assessment, but instead merely to convey an illustration of an example. Thus, use of any such terms should not be taken to limit the spirit and scope of embodiments of the present invention. The terms graph or graphical output may be construed to comprise a graph that is configured to be displayable in a user interface, but may also describe an input into a graphing system such that a graph may be created for display in the user interface. As such, the terms graph or graphical output may be used interchangeably herein.

In some example embodiments described herein, the apparatus, method and computer program product is configured to generate a graph having a scale (e.g. amplitude (y-axis) and/or time scale (x-axis)) that advantageously displays one or more data channels (e.g. a first or primary data channel, a secondary or related data channel and/or the like) that are derived from raw input data, one or more natural language text annotations and/or a narrative describing raw input data. As such, advantageously, a user viewing the graph, in a user interface or using other viewing means, may be provided with situational awareness with regard to the patterns shown on the graph as well as the events and or patterns that may have influenced the patterns shown on the graph.

Situational awareness may be defined as the perception of environmental elements with respect to time and/or space, the comprehension of their meaning, and the projection of their status after some variable has changed, such as time, or based on the happening of an event such as an alarm or alert. In other words, situational awareness is a state achieved when information that is qualitatively and quantitatively determined as suitable for particular purpose is made available to a user by engaging them in in an appropriate information exchange pattern or mental model. Situational awareness involves being aware of what is happening in the vicinity of a person or event to understand how information, events, and/or one's own actions may impact goals and objectives, both immediately and in the near future. Situational awareness may also be related to the perception of the environment critical to decision-makers in complex, dynamic areas from aviation, air traffic control, power plant operations, military command and control, engineering, machine monitoring, oil and gas, power plant monitoring, nuclear energy and emergency services such as firefighting and policing. Lacking or inadequate situational awareness has been identified as one of the primary factors in accidents attributed to human error. Accurate mental models are one of the prerequisites for achieving situational awareness. A mental model can be described as a set of well-defined, highly-organized yet dynamic knowledge structures developed over time from experience.

In some examples, a first or primary data channel may be selected for inclusion in a graph based on a selection by a user, via a user interface, may be selected based on the happening of a condition such as, but not limited to, an alert, an alarm, an anomaly, a violation of a constraint, a warning, a predetermined condition and/or the like. Alternatively or additionally the selection of the primary data channel may be determined based on the occurrence and/or detection of a pattern in the primary data channel.

In some example embodiments, a secondary or related data channel may also be selected. In some cases, there may be a plurality of secondary or related data channels. The secondary or related data channel may be selected for inclusion in a graph based on the detection of anomalous, unexpected or otherwise flagged behavior in the second or related channel. In some examples, the second or related channel is compared to one or more patterns in the primary data channel over a similar time period. For example, a first data channel may indicate a rise in heart rate, whereas a second data channel may indicate a stable or even a decline in respiration rate. Generally respiration rate rises with heart rate, and, as such, a stable respiration rate is generally unexpected. In some examples, unexpected behavior may lead to a life threatening condition, be indicative of a dangerous condition or the like.

Relationships between data channels may be defined as anomalous behavior by a qualitative model such as a domain model. A domain model is a representation of information about the domain. For example a domain model may contain an ontology that specifies the kinds of objects and concepts and the like that may exist in the domain in concrete or abstract form, properties that may be predicated of the objects and concepts and the like, relationships that may hold between the objects concepts and the like, and representations of any specific knowledge that is required to function in the domain. In some example multiple domain models may be provided for a single domain. Example domains may include, but are not limited to, medical, oil and gas, industrial, weather, legal, financial and/or the like. Alternatively or additionally, a plurality of related channels may be included, for example pulse rate, oxygen levels, blood pressure and/or the like.

In some examples, patterns (e.g. a trend, spike, step or the like) may be detected or otherwise identified in the primary data channel and/or in the one or more secondary data channels. Once a pattern is detected in the primary data channel and/or the one or more secondary data channels, an importance level or importance is assigned to each of the patterns. In the primary data channel an importance level may be defined based on thresholds, constraints, predefined conditions or the like. In the secondary data channels an importance level may also be assigned based on thresholds, constraints, predefined conditions or the like, however an importance level may also be assigned based on the relationship between the secondary data channels and the primary data channels and/or the relationships between the patterns detected in the primary data channels and the patterns detected in the secondary data channels. A pattern in the primary channel may be defined as a key pattern in an instance in which the importance level of the pattern exceeds or otherwise satisfies a predefined importance level. Likewise, a significant pattern is a pattern in a secondary data channel that exceeds or otherwise satisfies a predefined importance level. In some examples, a pattern in the one or more secondary channels may also be classified as a significant pattern if it represents an anomaly or otherwise unexpected behavior when compared with the primary data channel.

In some example embodiments, a contextual channel may also be selected. A contextual channel is a data channel that provides a background or circumstance information that may have caused or otherwise influenced the one or more key patterns and/or the one or more significant patterns (e.g. proximate cause). For example, a contextual channel may indicate an event, such as a medical treatment that was applied at the time of or just prior to the rise of the heartbeat and/or the fall or steady state of the respiration rate. Alternatively or additionally, a plurality of data channels may also be selected for inclusion in a graph based on an anomaly or unexpected behavior.

Alternatively or additionally, one or more data channels may be selected for inclusion in a graph even though the one or more data channels are representative of expected behavior. For example, in the medical domain, a medical professional may expect to see both heart rate and respiration rate on a graph even if both are behaving in expected ways, since expected behavior may be indicative of an important result, namely a clean bill of health.

In yet further example embodiments, events may also be generated for display in the graph. An event may be described in a contextual channel, may be entered into an event log that is input with the raw input data or may be inferred. For example, caffeine administration may be entered as an explicit event in a patient record (e.g. in an event log), the caffeine could be detected by a change in one or data channels which record what medication is being administered through an IV line and/or the caffeine administration may be inferred based on a spike in heart rate. In instances in which an event is identified that satisfies an importance threshold, the event may be displayed as a visual annotation. In an example in which a graph is displayed, events may be displayed as a vertical line (see e.g., FIG. 2). Alternatively or additionally events may be generated as a horizontal line with indicators showing the multiple occurrences of an event and/or the like. In other visualizations, events may be displayed via text, indicator or other visual outputs.

In some example embodiments, a scale may be selected for the graph based on the primary data channel, the secondary data channel or the like. The scale may be determined based on a time period or duration in which a pattern that satisfies an importance threshold is identified, anomalous behavior occurs in a related data channel and/or the like. Alternatively or additionally the time period may be set by a user, may be a time period that is significant or specifically identified on the basis of properties of the domain, or the like.

In further example embodiments, textual annotations and/or a narrative may be included with the graph. The textual annotations and/or the narrative may be provided by a natural language generation system that is configured to generate one or more textual annotations in the form of sentences or phrases that describe the patterns in the data channels, expected or unexpected behavior, an event, a contextual channel and/or the like. Additionally, in some examples, the sentences or phrases may take the form of stand-alone text that provides situational awareness and/or situational analysis of the graph. In some examples, situation analysis text may be configured to include pattern descriptions that contribute to narrative coherence, background information or the like. The textual annotations may be located on the graph, such as at the location where the anomalies and/or the patterns are represented in the graph. Alternatively or additionally, the narrative or situational awareness text may be displayed on or near the graph in some examples. Whereas, in other examples, the narrative or situational text may be contained in a separate file or may be generated before/after or otherwise separately from the generation of the graph. Alternatively or additionally, the textual annotations and/or narrative may be provided via speech or other available modalities.

Based on the one or more channels derived from the raw input data, the contextual channel and/or the annotations, the systems and methods described herein are configured to generate a graph for display. The graph is configured to display a time scale that contains those identified sections (e.g. key patterns and/or significant patterns) in the one or more data channels, the textual annotations, additional available visual annotations and/or the like. In some example embodiments, user interaction with the narrative text may result in an annotation on the graphical output to be highlighted. Similarly selection of an annotation may highlight narrative text related to the annotation. Alternatively or additionally, the annotations may include a symbol or other reference numeral that is indicative of or otherwise related to the narrative. For example, the narrative may indicate that a first key pattern is indicated by an arrow, a circle, a box, a reference number or the like in the graph.

FIG. 1 is an example block diagram of example components of an example graphical annotation environment 100. In some example embodiments, the graphical annotation environment 100 comprises a data analyzer 102, a data interpreter 104, a graphical annotation engine 106, a natural language generation system 108 and one or more data sources, such as but not limited to, raw input data 110, an event log 112 and a domain model 114. In some example embodiments, historical data may also be accessed and/or otherwise analyzed. The data analyzer 102, a data interpreter 104, graphical annotation engine 106, a natural language generation system 108 make take the form of, for example, a code module, a component, circuitry or the like. The components of the graphical annotation environment 100 are configured to provide various logic (e.g. code, instructions, functions, routines and/or the like) and/or services related to the generation and/or annotation of a graphical output.

In some example embodiments, the data analyzer 102 is configured to input raw data, such as the raw data contained in the raw input data 110. The receipt or input of the raw input data may occur in response to an alarm condition (e.g. an alarm received from a source such as, but not limited to, another system, another monitoring system or the like), a violation of a constraint (e.g. a data value over a threshold, within a threshold for a period of time and/or the like), a user input or the like. Alternatively or additionally the data analyzer 102 may be configured to receive or input raw input data continuously or semi-continuously, such as via a data stream, and determine an importance of the raw input data (e.g., whether the data violates a constraint, satisfies a threshold and/or the like).

Raw input data may include data such as, but not limited to, time series data that captures variations across time (e.g. profits, rainfall amounts, temperature or the like), spatial data that indicates variation across location (e.g. rainfall in different regions), or spatial-temporal data that combines both time series data and spatial data (e.g. rainfall across time in different geographical output areas). The raw input data contained or otherwise made accessible by the raw input data 110 may be provided in the form of numeric values for specific parameters across time and space, but the raw input data may also contain alphanumeric symbols, such as the RDF notation used in the semantic web, or as the content of database fields. The raw input data 110 may be received from a plurality of sources and, as such, data received from each source, sub source or data that is otherwise related may be grouped into or otherwise to referred to as a data channel.

The data analyzer 102 is configured to detect patterns and trends in the one or more data channels that are derived from the raw input data to provide a set of abstractions from the raw input data in the data channels. For example, a time-series dataset may contain tens of thousands of individual records describing the temperature at various points on a component piece of machinery over the course of a day with a sample once every two or three seconds. Trend analysis may then be used to identify that the temperature changes in a characteristic way throughout certain parts of the day. As such, trend analysis is configured to abstract those changes into an abstraction that is representative of the change over time. In some example embodiments, the data analyzer 102 may be configured to fit a piecewise linear model to the data received in the primary data channel, related data channel or the like.

In some example embodiments, the data analyzer 102 is further configured to determine a first or primary data channel. The primary data channel is generally related, for example, to the raw input data and/or the data channel having data values that caused or otherwise related to the alarm condition, a data channel identified by a user action or a data channel that has otherwise been provided to the data analyzer 102. In some example embodiments, the data analyzer 102 may also be configured to identify data channels that are related to the primary data channel. Alternatively or additionally, relations between data channels may be defined by the domain model 114 and input into the data analyzer 102.

The data analyzer 102 may then identify trends, spikes, steps or other patterns in the data channels to generate abstractions that summarize the patterns determined in the primary data channel and/or the other related data channels. Alternatively or additionally, the data analyzer 102 may also be configured to perform pattern detection on the raw input data irrespective of data channels or the receipt of an alarm condition.

A data interpreter, such as data interpreter 104, may then be configured to input the abstractions and determine an importance level and/or relationships between the abstractions identified in the one or more data channels. In order to determine the importance level and relationships, the data interpreter 104 may access the domain model 114 directly or indirectly via the data analyzer 102 or the like. The domain model 114 may contain information related to a particular domain or industry. In some examples, the domain model 114 may provide single data channel limits related to normal behaviors in a domain (e.g. normal ranges), information related to anomalous behaviors and/or the like. In other examples the domain model 114 may describe relationships between various events and/or phenomena in multiple data channels. For example in a weather domain, a domain model may include wind speeds that are related to hurricane type events or temperatures that may cause harm to humans or other animals or may cause damage or interference to shipping. Extreme weather events may be labeled as important, whereas typical temperatures may not be marked as important.

In some example embodiments, the data interpreter 104 may be configured to determine the importance of the one or more detected patterns in the primary data channel, such as by using the domain model 114. The data interpreter 104 may assign an importance level based on the pattern itself (e.g. magnitude, duration, rate of change or the like), defined constraints (e.g. defined thresholds or tolerances), temporal relationships between the pattern in the primary data channel and patterns in other related data channels and/or the like. For example, a heart rate over 170 beats per minute, or 100 mile per hour winds, may be assigned a high level of importance. In some examples, the patterns and/or the constraints may be defined by the domain model 114.

Using the importance level, the data interpreter 104 may assign certain ones of the patterns as key patterns. A key pattern may be selected based on a pre-determined importance level, such as a threshold defined by a user or a constraint defined by the domain model 114. Alternatively or additionally, key patterns may be selected based on those patterns in the primary data channel with the highest level of importance, based on the alarm condition and/or the like. For example any wind readings over 50 miles per hour may be designated as key patterns, whereas in other examples only the highest wind reading over a time period may be a determined to be a key pattern. In other examples, the importance level determination may be performed over a plurality of time scales that may be user defined (e.g., one hour, one day, one week, one month and/or the like).

In some example embodiments, the data interpreter 104 may also be configured to determine the importance of patterns detected in one or more secondary or related data channels. In some examples, the data interpreter 104 may determine one or more patterns in the related data channels that overlap time-wise or occur within the same time period as the patterns in the primary data channel. The data interpreter 104 may then mark the one or more patterns in the related channels as expected, unexpected or as having or not having some other property using the domain model 114. For example, the domain model may suggest that the one or more patterns in the related data channel were expected to rise as they did in the primary channel. By way of example, as winds are rising, a wave height may then be expected to rise. In other cases the behavior of the one or more related channels may be unexpected or may be anomalous when compared to the behavior of the primary data channel.

The data interpreter 104 may is configured to instantiate a plurality of messages based on the raw input data derived from the key events, the significant events, the primary data channel, the one or more related data channels, the historical data, the events (e.g. in the event log 112), the contextual channel and/or the like. In order to determine the one or more messages, the importance level of each of the messages and relationships between the messages, the data interpreter 104 may be configured to access the domain model 104 directly or indirectly via the data analyzer 102 or the like.

In some examples, messages are language independent data structures that correspond to informational elements in a text and/or collect together underling data in such a way that the underlying data can be linguistically expressed. In some examples, messages are created based on a requirements analysis as to what is to be communicated for a particular scenario (e.g. for a particular domain). A message typically corresponds to a fact about the underlying data (for example, the existence of some observed event) that could be expressed via a simple sentence (although it may ultimately be realized by some other linguistic means). For example, to linguistically describe wind, a user may want to know a speed, a direction, a time period or the like, but also the user wants to know changes in speed over time, warm or cold fronts, geographic areas and or the like. In some cases, users do not even want to know wind speed, they simply want an indication of a dangerous wind condition. Thus, a message related to wind speed may include fields to be populated by data related to the speed, direction, time period or the like, and may have other fields related to different time points, front information or the like. The mere fact that wind exists may be found in the data, but to linguistically describe "light wind" or "gusts" different data interpretation must be undertaken as is described herein.

The one or more patterns may be marked as significant patterns based on the domain model 114. For example, patterns in the related data channel that have an importance level above a predetermined threshold defined by the domain model 114 may be marked as significant patterns. In some example embodiments, unexpected patterns are also categorized as significant patterns as they are suggestive of a particular condition or fault. Other patterns may be determined to be significant patterns based on one or more constraints on channel value (e.g. expected range of values or the like), data anomalies, patterns marked as neither expected or unexpected that satisfy an importance level, and/or the like.

In further example embodiments, the data interpreter 104 may be configured to determine and/or infer one or more events from the one or more data channels. Events may include specific activities that may influence the one or more key patterns and/or may have caused the one or more significant patterns. In some examples, the one or more events may be inferred based in context with the one or more patterns in the primary data channel. Alternatively or additionally events may be provided as a separate channel, such as a contextual channel, in the raw input data 110 or may be provided directly, such as in an event log 112, to the data interpreter 104.

The one or more key patterns and the one or more significant patterns may be input into the graphical annotation engine 106 and the natural language generation system 108 to enable the generation of a graphical output and/or natural language annotations. In some example embodiments, the graphical annotation engine 106 is configured to generate a graphical output having one or more textual annotations, such as the graphical output displayed with reference to FIG. 2. The graphical output and the one or more textual annotations are configured to be generated by one or more of a scale determination engine 120, an annotation location determiner 122 and a graphical output generator 124.

In some example embodiments the scale determination engine 120 is configured to determine a time scale (e.g. x-axis) to be used in the graphical output. The scale determination engine 120 may determine a time period that captures or otherwise includes one or more of the key patterns. In some example embodiments, the time period may be chosen based on the highest number of key patterns, whereas in other embodiments the time scale chosen may include each of the one or more key patterns and/or each of the one or more significant patterns. Alternatively or additionally, the scale determination engine 120 may also determine a scale for the amplitude or y-axis of the graph.

An annotation location determiner 122 is configured to place one or more annotations, such as textual or visual annotations, on a graphical output produced by the graphical output generator 124. As is described herein, natural language annotations may be generated, such as by the natural language generation system 108, to explain or otherwise describe the one or more key patterns in the primary data channel. In an instance in which the data interpreter 104 determines one or more significant patterns, natural language annotations may also be generated to explain the one or more significant patterns in the related data channels.

The annotation location determiner 122 is further configured to place an annotation on the graphical output in the proximity of the key pattern or the significant pattern. In other example embodiments, the annotations may otherwise be linked to the graphical output by using reference lines, highlights or other visual indications on or around the graphical output.

In some example embodiments a natural language generation system, such as natural language generation system 108, is configured to generate phrases, sentences, text or the like which may take the form of natural language annotations. Other linguistic constructs may be generated in some example embodiments. The natural language generation system 108 comprises a document planner 130, a microplanner 132 and/or a realizer 134. Other natural language generation systems may be used in some example embodiments, such as a natural language generation system as described in Building Natural Language Generation Systems by Ehud Reiter and Robert Dale, Cambridge University Press (2000), which is incorporated by reference in its entirety herein.

The document planner 130 is configured to input the one or more patterns from the data interpreter in the form of messages and determine how to use those messages to describe the patterns in the one or more data channels derived from the raw input data. The document planner 130 may comprise a content determination process that is configured to select the messages, such as the messages that describe the key patterns and/or the significant patterns, that are be displayed in the graphical output by the graphical annotation engine 106. In some examples the content determination process may be related to or otherwise limited by the scale determined by the scale determination engine 120. The document planner 130 may also comprise a structuring process that determines the order of messages referring to the key patterns and/or significant patterns to be included in a narrative and/or the natural language annotations.

In some example embodiments, the document planner 130 may access one or more text schemas for the purposes of content determination and document structuring. A text schema is a rule set that defines the order in which a number of messages are to be presented in a document. For example, an event (e.g. medication injection) may be described prior to a key pattern (e.g. rise in heart rate). In other examples, a significant pattern (e.g. falling or steady respiratory rate) may be described after, but in relation to, a description of the key pattern (e.g. rise in heart rate). The output of the document planner 130 may be a tree-structured object or other data structure that is referred to as a document plan. In an instance in which a tree-structured object is chosen for the document plan, the leaf nodes of the tree may contain the messages, and the intermediate nodes of the tree structure object may be configured to indicate how the subordinate nodes are related to each other.

The microplanner 132 is configured to modify the document plan from the document planner 130, such that the document plan may be expressed in natural language. In some example embodiments, the microplanner 132 may perform aggregation, lexicalization and referring expression generation. In some examples, aggregation includes, but is not limited to, determining whether two or more messages can be combined together linguistically to produce a more complex sentence. For example, one or more key patterns may be aggregated so that both of the key patterns can be described by a single sentence. Alternatively or additionally, aggregation may not be performed in some instances so as to enable stand-alone interpretation if a portion of the natural language text is shown as an annotation independently on a graphical output.

In some examples, lexicalization includes, but is not limited to, choosing particular words for the expression of concepts and relations. In some examples, referring expression generation includes, but is not limited to, choosing how to refer to an entity so that it can be unambiguously identified by the reader. The output of the microplanner 132, in some example embodiments, is a tree-structured realization specification whose leaf-nodes are sentence plans, and whose internal nodes express rhetorical relations between the leaf nodes.

The realizer 134 is configured to traverse the tree-structured realization specification to express the tree-structured realization specification in natural language. The realization process that is applied to each sentence plan makes use of a grammar which specifies the valid syntactic structures in the language and further provides a way of mapping from sentence plans into the corresponding natural language sentences. The output of the process is, in some example embodiments, a well-formed natural language text. In some examples, the natural language text may include embedded mark-up. The output of the realizer 134, in some example embodiments, is the natural language annotations that are configured to be on or in proximity to a graphical output. The realizer may also output situational analysis text or a narrative that is configured to describe or otherwise summarize the one or more key patterns, the one or more significant patterns, the one or more contextual channels, and/or the one or more events to be displayed in the graphical output. Alternatively or additionally, the natural language annotations and/or the narrative may describe data that is not included on the graph to provide additional situational awareness.

The graphical output generator 124 is configured to generate a graphical output within the determined scale. Thus, the graphical output includes the raw input data for the primary data channel and/or any related data channels within the determined scale. The graphical output generator 124 is further configured to display the natural language annotations on the graphical output as well as a narrative that describes the data channels displayed in the graphical output. In some example embodiments, the natural language annotations may be interactively linked to the graphical output. For example, phrases within the narrative may be underlined or otherwise highlighted such that in an instance in which the underlined or otherwise highlighted phrases are selected, a natural language annotation may be shown or otherwise emphasized on the graphical output. Alternatively or additionally, by selecting a natural language annotation on the graphical output, the graphical output generator in conjunction with a user interface may underline or otherwise highlight a corresponding phrase in the narrative. Alternatively or additionally, other visualizations may be provided by the graphical output generator 124 in conjunction with or in replacement of the graph or graphical output, such as, but not limited to, a visual image, a video, a chart and/or the like.

FIG. 2 illustrates an example graphical output having multiple data channels in accordance with some example embodiments of the present invention. FIG. 2 provides a graphical output that visually represents the behavior of heart rate and respiration rate in response to an application of caffeine over a period of time. The following example table (e.g. raw input data) illustrates a primary data channel (e.g. heart rate) and a related data channel (e.g. respiration rate):

| Time | Heart Rate | Respiration Rate |
|---|---|---|
| 1 | 68 | 14 |
| 2 | 72 | 15 |
| 3 | 70 | 14 |
| 4 | 70 | 14 |
| 5 | 69 | 16 |
| 6 | 72 | 15 |
| 7 | 73 | 16 |
| 8 | 68 | 13 |
| 9 | 70 | 14 |
| 10 | 71 | 15 |
| 11 | 90 | 14 |
| 12 | 110 | 14 |
| 13 | 118 | 14 |
| 14 | 116 | 15 |
| 15 | 105 | 15 |
| 16 | 92 | 14 |
| 17 | 86 | 13 |
| 18 | 80 | 14 |
| 19 | 75 | 14 |
| 20 | 72 | 15 |
| 21 | 70 | 14 |
| 22 | 71 | 13 |
| 23 | 69 | 13 |
| 24 | 71 | 14 |

As is illustrated in the table above, there is a rapid change of heart rate between time point 10 and time point 11 indicating a change in condition. As such, a data analyzer 102, a data interpreter 104 and/or the like may receive an indication of an alarm condition, may determine that such a spike is representative of an alarm condition, may receive an indication by the user or the like. In response, the data analyzer 102, the data interpreter 104 or the like may cause the heart rate data channel to be selected as the primary data channel. In other embodiments, a user, domain knowledge or the like may indicate that the heart rate channel is selected to be the primary data channel.

In an instance in which a primary data channel is identified, in this case heart rate, the data analyzer 102, a data interpreter 104 and/or the like may determine whether one or more key patterns are present in the primary data channel 212. In this example, a key pattern may be the rapid change of heart rate between time point 10 and time point 11, but it may also include the rise and fall (e.g. spike) of the heart rate between time points 10 and 19, with the high point being at time point 13. In some examples, there may be multiple key patterns in the primary data channel.

The data interpreter 104 may then determine whether there is a secondary or related data channel that contains a significant pattern, such as secondary channel 216 (e.g. respiration rate), that has a significant pattern (e.g. no change when a change is generally expected) in a corresponding time period. As described herein, the corresponding time period may be the same time period or may be a later time period when compared to the time period of the key patterns. Further, the corresponding time period may, in some examples, be defined by a domain model, such as domain model 114.

The data analyzer 102, a data interpreter 104 and/or the like may access data related to the respiration rate of the patient during the same or similar time period. Upon reviewing the corresponding data, the data analyzer 102, the data interpreter 104 and/or the like may determine that the secondary channel 216 was relatively flat and, based on the domain model, such a behavior was unexpected. As described herein, unexpected behavior in a related data channel is a significant pattern. Thus, FIG. 2 provides a key pattern, namely the heart rate change between time periods 10 and 19 and a significant pattern represented by the relatively steady respiration rate over the same time period. FIG. 2 further comprises an event 220 that was derived from a contextual channel, an event log or the like. The event 220 corresponds to the application of caffeine in this example.

The natural language generation system 108 may input the primary data channel, the secondary data channel, the contextual channel, events, and/or the like. As such, the natural language generation system 108 may be configured to generate a narrative, such as narrative 224, and one or more textual annotations, such as textual annotations 214, 218 and 222. In some examples, the textual annotations are configured to describe the one or more key patterns, the one or more significant patterns, the one or more events, the contextual channel or the like.

The graphical annotation engine 106 may input the key pattern and the significant pattern and may determine a time scale for the graph, such as by the scale determination engine 120. In FIG. 2, the scale chosen is configured to highlight the key pattern, the significant pattern and the caffeine event. Based on the scale, the primary and secondary data channels are represented graphically by the graphical output generator 124. The annotation location determiner 122 may locate the key pattern, significant pattern and/or event on the graph and then may assign a location of a textual annotation in a nearby area, such as is shown in FIG. 2. One or more text annotations, such as textual annotations 214, 218 and 222 may then be added to the graph in conjunction with a narrative 224.

FIG. 3 is an example block diagram of an example computing device for practicing embodiments of an example graphical annotation environment. In particular, FIG. 3 shows a computing system 300 that may be utilized to implement a graphical annotation environment 100 having a data analyzer 102, a data interpreter 104, a graphical annotation engine 106, a natural language generation system 108 and/or a user interface 310. One or more general purpose or special purpose computing systems/devices may be used to implement the data analyzer 102, the data interpreter 104, the graphical annotation engine 106, the natural language generation system 108 and/or the user interface 310. In addition, the computing system 300 may comprise one or more distinct computing systems/devices and may span distributed locations. For example, in some embodiments, the natural language generation system 108 may be accessible remotely via the network 350. In other example embodiments, one or more of the data analyzer 102, the data interpreter 104, the graphical annotation engine 106, the natural language generation system 108 and/or the user interface 310 may be configured to operate remotely. In some example embodiments, a pre-processing module or other module that requires heavy computational load may be configured to perform that computational load and thus may be on a remote device or server. For example, the data analyzer 102 and/or the data interpreter 104 may be accessed remotely. Furthermore, each block shown may represent one or more such blocks as appropriate to a specific example embodiment. In some cases one or more of the blocks may be combined with other blocks. Also, the data analyzer 102, the data interpreter 104, the graphical annotation engine 106, the natural language generation system 108 and/or the user interface 310 may be implemented in software, hardware, firmware, or in some combination to achieve the capabilities described herein.

In the example embodiment shown, computing system 300 comprises a computer memory ("memory") 301, a display 302, one or more processors 303, input/output devices 304 (e.g., keyboard, mouse, CRT or LCD display, touch screen, gesture sensing device and/or the like), other computer-readable media 305, and communications interface 306. The processor 303 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 3 as a single processor, in some embodiments the processor 303 comprises a plurality of processors. The plurality of processors may be in operative communication with each other and may be collectively configured to perform one or more functionalities of the graphical annotation environment as described herein.

The data analyzer 102, the data interpreter 104, the graphical annotation engine 106, the natural language generation system 108 and/or the user interface 310 are shown residing in memory 301. The memory 301 may comprise, for example, transitory and/or non-transitory memory, such as volatile memory, non-volatile memory, or some combination thereof. Although illustrated in FIG. 3 as a single memory, the memory 301 may comprise a plurality of memories. The plurality of memories may be embodied on a single computing device or may be distributed across a plurality of computing devices collectively configured to function as the graphical annotation environment. In various example embodiments, the memory 301 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof.

In other embodiments, some portion of the contents, some or all of the components of the data analyzer 102, the data interpreter 104, the graphical annotation engine 106, the natural language generation system 108 and/or the user interface 310 may be stored on and/or transmitted over the other computer-readable media 305. The components of the data analyzer 102, the data interpreter 104, the graphical annotation engine 106, the natural language generation system 108 and/or the user interface 310 preferably execute on one or more processors 303 and are configured to generate graphical annotations, as described herein.

Alternatively or additionally, other code or programs 330 (e.g., an administrative interface, a Web server, and the like) and potentially other data repositories, such as data repository 340, also reside in the memory 301, and preferably execute on one or more processors 303. Of note, one or more of the components in FIG. 3 may not be present in any specific implementation. For example, some embodiments may not provide other computer readable media 305 or a display 302.

In some example embodiments, as described above, the graphical annotation engine 106 may comprise a scale determination engine 120, an annotation location determiner 122, a graphical output generator 124 or the like. The natural language generation system 108 may comprise a document planner 130, a microplanner 132, a realizer 134 and/or the like. In some example embodiments, the data analyzer 102, the data interpreter 104, the graphical annotation engine 106, the natural language generation system 108 and/or the user interface 310 may also include or otherwise be in data communication with raw input data 110, event log 112 and/or the domain model 114. The data analyzer 102, the data interpreter 104, the graphical annotation engine 106, the natural language generation system 108 and/or the user interface 310 are further configured to provide functions such as those described with reference to FIG. 1.

The data analyzer 102, the data interpreter 104, the graphical annotation engine 106, the natural language generation system 108 and/or the user interface 310 may interact with the network 350, via the communications interface 306, with remote data sources 356 (e.g. remote reference data, remote performance data, remote aggregation data and/or the like), third-party content providers 354 and/or client devices 358. The network 350 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX, Bluetooth) that facilitate communication between remotely situated humans and/or devices. In some instance the network 350 may take the form of the interne or may be embodied by a cellular network such as an LTE based network. In this regard, the communications interface 306 may be capable of operating with one or more air interface standards, communication protocols, modulation types, access types, and/or the like. The client devices 358 include desktop computing systems, notebook computers, mobile phones, smart phones, personal digital assistants, tablets and/or the like.

In an example embodiment, components/modules of the data analyzer 102, the data interpreter 104, the graphical annotation engine 106, the natural language generation system 108 and/or the user interface 310 are implemented using standard programming techniques. For example, the data analyzer 102, the data interpreter 104, the graphical annotation engine 106, the natural language generation system 108 and/or the user interface 310 may be implemented as a "native" executable running on the processor 303, along with one or more static or dynamic libraries. In other embodiments, the data analyzer 102, the data interpreter 104, the graphical annotation engine 106, the natural language generation system 108 and/or the user interface 310 may be implemented as instructions processed by a virtual machine that executes as one of the other programs 330. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use synchronous or asynchronous client-server computing techniques. Also, the various components may be implemented using more monolithic programming techniques, for example, as an executable running on a single processor computer system, or alternatively decomposed using a variety of structuring techniques, including but not limited to, multiprogramming, multithreading, client-server, or peer-to-peer, running on one or more computer systems each having one or more processors. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the data analyzer 102, the data interpreter 104, the graphical annotation engine 106, the natural language generation system 108 and/or the user interface 310, such as by using one or more application programming interfaces can be made available by mechanisms such as through application programming interfaces (API) (e.g. C, C++, C#, and Java); libraries for accessing files, databases, or other data repositories; through scripting languages such as XML; or through Web servers, FTP servers, or other types of servers providing access to stored data. The raw input data 110, the event log 112 and the domain model 114 may be implemented as one or more database systems, file systems, or any other technique for storing such information, or any combination of the above, including implementations using distributed computing techniques. Alternatively or additionally, the raw input data 110, the event log 112 and the domain model 114 may be local data stores but may also be configured to access data from the remote data sources 356.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the data analyzer 102, the data interpreter 104, the graphical annotation engine 106, the natural language generation system 108 and/or the user interface 310 may be implemented or provided in other manners, such as at least partially in firmware and/or hardware, including, but not limited to one or more ASICs, standard integrated circuits, controllers executing appropriate instructions, and including microcontrollers and/or embedded controllers, FPGAs, complex programmable logic devices ("CPLDs"), and the like. Some or all of the system components and/or data structures may also be stored as contents (e.g., as executable or other machine-readable software instructions or structured data) on a computer-readable medium so as to enable or configure the computer-readable medium and/or one or more associated computing systems or devices to execute or otherwise use or provide the contents to perform at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

FIGS. 4-6 illustrate example flowcharts of the operations performed by an apparatus, such as computing system 300 of FIG. 3, in accordance with example embodiments of the present invention. It will be understood that each block of the flowcharts, and combinations of blocks in the flowcharts, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory 301 of an apparatus employing an embodiment of the present invention and executed by a processor 303 in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 4-6, when executed, convert a computer or processing circuitry into a particular machine configured to perform an example embodiment of the present invention. Accordingly, the operations of FIGS. 4-6 define an algorithm for configuring a computer or processor, to perform an example embodiment. In some cases, a general purpose computer may be provided with an instance of the processor which performs the algorithm of FIGS. 4-6 to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowcharts', and combinations of blocks in the flowchart, can be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included (some examples of which are shown in dashed lines in FIG. 4). It should be appreciated that each of the modifications, optional additions or amplifications described herein may be included with the operations herein either alone or in combination with any others among the features described herein.

FIG. 4 is a flow chart illustrating an example method for generating graphical annotations. As is shown in operation 402, an apparatus may include means, such as the data analyzer 102, the graphical annotation engine 106, the processor 303, or the like, for receiving an indication of an alarm condition. In some example embodiments an alarm may cause the selection of a primary data channel and a determination of a time period in which the alarm was generated. Alternatively or additionally other means may be used to alert the apparatus to a primary data channel, such as, but not limited to, a user action, a detected pattern in the raw input data or a data channel, a determined value in the raw input data or a data channel, and/or the like.

As is shown in operation 404, an apparatus may include means, such as the data analyzer 102, the data interpreter 104, the processor 303, or the like, for determining one or more key patterns in a primary data channel. In some example embodiments the key patterns may be determined based on the time period of the alarm condition, however in other examples a larger or smaller time period may be selected. The determination of the one or more key patterns is further described with reference to FIG. 5.

As is shown in operation 406, an apparatus may include means, such as the data analyzer 102, the data interpreter 104, the processor 303, or the like, for determining one or more significant patterns in one or more related data channels. In some example embodiments, the apparatus, such as via the data analyzer 102 may determine one or related channels based on one or more predefined relationships. In some examples, the predefined relationships may be defined by the domain model 114. The determination of the one or more significant patterns is further described with reference to FIG. 6.

As is shown in operation 408, an apparatus may include means, such as the data analyzer 102, the data interpreter 104, the processor 303, or the like, for determining one or more contextual channels to be included in the graphical output. The one or more contextual channels may provide events or other context that may be indicative of the cause of the one or more key patterns and/or the one or more significant patterns. As is shown in operation 410, an apparatus may include means, such as the graphical annotation engine 106, the scale determination engine 120, the processor 303, or the like, for determining a time period to be represented by the graphical output. In some example embodiments, the time period chosen for the graph is the time period in which the one or more key patterns are displayed. As is shown in operation 412, an apparatus may include means, such as the natural language generation system 108, the document planner 130, the microplanner 132, the realizer 134, the processor 303, or the like, for generating a natural language annotation of at least one of the one or more key patterns or the one or more significant patterns.

As is shown in operation 414, an apparatus may include means, such as the graphical annotation engine 106, the annotation location determiner 122, the graphical output generator 124, the processor 303, the user interface 310 or the like, for generating a graphical output that is configured to be displayed in a user interface. In some example embodiments, the graph is configured to utilize the determined scale to display the primary data channel, one or more related channels having significant events, natural language annotations, a narrative, events and/or the like. In some example embodiments and in an instance in which a user clicks on a text annotation in the graph, a corresponding phrase in the situation analysis text may be highlighted and/or in an instance in which a user clicks on underlined phrase in the narrative or situation analysis text, a corresponding annotation may be highlighted on the graph.

FIG. 5 is a flow chart illustrating an example method determining one or more key patterns in a primary data channel. As is shown in operation 502, an apparatus may include means, such as the data analyzer 102, the data interpreter 104, the processor 303, or the like, for identifying one or more patterns wherein a pattern is at least one of a trend, spike or step in the data channel. As is shown in operation 504, an apparatus may include means, such as the data analyzer 102, the data interpreter 104, the processor 303, or the like, for assigning an importance level to the one or more patterns. As is shown in operation 506, an apparatus may include means, such as the data analyzer 102, the data interpreter 104, the processor 303, or the like, for identifying one or more key patterns of the one or more patterns, wherein a key pattern is a pattern that exceeds a predefined importance level.

FIG. 6 is a flow chart illustrating an example method determining one or more significant patterns in a related data channel. As is shown in operation 602, an apparatus may include means, such as the data analyzer 102, the data interpreter 104, the processor 303, or the like, for identifying one or more unexpected patterns in a related data channel in response to detecting one or more patterns in the data channel. In some example embodiments, the one or more patterns identified in another data channel violate a predetermined constraint, threshold or the like may be considered as unexpected patterns or anomalies. The one or patterns may be identified within the time period or scale identified for the graph. As is shown in operation 604, an apparatus may include means, such as the data analyzer 102, the data interpreter 104, the processor 303, or the like, for assigning an importance level to the one or more unexpected patterns. As is shown in operation 606, an apparatus may include means, such as the data analyzer 102, the data interpreter 104, the processor 303, or the like, for identifying one or more significant patterns of the one or more unexpected patterns, wherein a significant pattern is an unexpected pattern.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A computer-implemented method for transforming raw input data that is at least partially expressed in a non-linguistic format into a format that can be expressed linguistically in one or more phrases with a graphical representation of the raw input data, the method comprising:
   detecting, by a processor, one or more patterns in a data channel derived from raw input data;
   identifying, by the processor, one or more patterns in another data channel also derived from the raw input data;
   determining, by the processor, from one or more contextual channels context information for at least one of the one or more patterns in the data channel or the one or more patterns in the another data channel;
   generating, using a natural language generation system that is configured to execute on the processor, one or more phrases describing the one or more patterns in the data channel and the one or more patterns in the another data channel, the one or more phrases generated by:
      generating at least one message when a pattern from the one or more patterns in the data channel or a pattern from the one or more patterns in the another data channel satisfies one or more message requirements,
      selecting one or more words to express a concept or a relation in the at least one message, and
      applying a grammar to the selected one or more words; and
   generating, using the processor, a graphical output for display in a user interface, based on the data channel, the another data channel, the one or more contextual channels, and the one or more phrases, wherein the one or more phrases are interactively annotated on the graphical output of the data channel and the another data channel.

2. A method according to claim 1, further comprising:
   detecting, by the processor, one or more patterns in the data channel by:
   identifying, by the processor, one or more patterns wherein a pattern is at least one of a trend, spike or step in the data channel;
   assigning, by the processor, an importance level to the one or more patterns; and
   identifying, by the processor, one or more key patterns of the one or more patterns, wherein a key pattern is a pattern that exceeds a predefined importance level.

3. A method according to claim 2, further comprising:
   determining, by the processor, a time period to be displayed in a graph, wherein the time period chosen for the graph is the time period in which the one or more key patterns are displayed.

4. A method according to claim 3, further comprising:
   identifying, by the processor, one or more patterns in the another data channel by:
   assigning, by the processor, an importance level to one or more unexpected patterns; and
   identifying, by the processor, one or more significant patterns of the one or more unexpected patterns, wherein a significant pattern is an unexpected pattern.

5. A method according to claim 4, further comprising:
   determining, by the processor, that the one or more patterns identified in an another data channel violate a predetermined constraint; and
   determining, by the processor, that the one or more patterns are one or more unexpected patterns.

6. A method according to claim 4, wherein the one or more unexpected patterns are identified within the time period of the graph.

7. A method according to claim 4, further comprising:
   generating, by the processor, the graph based on the graphical output, wherein the graph comprises at least a portion of the data channel that contains the one or more key events, the another data channel that contains the one or more significant events and the one or more contextual channels, the at least a portion of the one or more key events, the one or more significant events and the one or more contextual channels being annotated by the one or more phrases;
   generating, by the processor, a narrative; and
   causing, by the processor, the graph to be displayed in a user interface.

8. A method according to claim 7, wherein additional information related to the one or more phrases is displayed in response to a user interaction with the user interface.

9. A method according to claim 7, wherein the one or more key patterns and the one or more significant patterns are highlighted in response to a user interaction with the one or more phrases in the user interface.

10. A method according to claim 1, wherein the context information provides at least background or circumstance information having influenced the one or more patterns in the data channel or the one or more patterns in the another data channel.

11. A method according to claim 1, wherein the data channel is selected from one or more data channels derived from the raw input data, the data channel is selected based on an indication received from at least one of a user, an alarm or another computing device.

12. A method according to claim 1, further comprising:
   receiving, by the processor, an indication of a determined scale from a user via a user interface; and
   generating, by the processor, the graphical output based on the data channel, the another data channel and the one or more phrases in accordance with the determined scale.

13. A method according to claim 1, further comprising:
   receiving, by the processor, a selection of one or more of the primary data channel, the another data channel, or a contextual channel from a user via a user interface; and generating, by the processor, the graphical output for display in the user interface, based on the selection of the one or more of the primary data channel, the another data channel, or the contextual channel and the natural language annotation for the selection.

14. An apparatus comprising:
at least one processor; and
at least one memory including computer program code, the at least one memory and the computer program code configured to, with the at least one processor, cause the apparatus to at least:
detect one or more patterns in a data channel derived from raw input data;
identify one or more patterns in another data channel also derived from the raw input data;
determine from one or more contextual channels context information for at least one of the one or more patterns in the data channel or the one or more patterns in the another data channel;
generate, using a natural language generation system that is configured to execute on a processor, one or more phrases describing the one or more patterns in the data channel and the one or more patterns in the another data channel, the one or more phrases generated by:
generating at least one message when a pattern from the one or more patterns in the data channel or a pattern from the one or more patterns in the another data channel satisfies one or more message requirements,
selecting one or more words to express a concept or a relation in the at least one message, and
applying a grammar to the selected one or more words; and
generate a graphical output, for display in a user interface, based on the data channel, the another data channel, the one or more contextual channels, and the one or more phrases, wherein the one or more phrases are interactively annotated on the graphical output of the data channel and the another data channel.

15. An apparatus according to claim 14, wherein the at least one memory including the computer program code is further configured to, with the at least one processor, cause the apparatus to:
identify one or more patterns in the primary data channel;
assign an importance level to the one or more patterns; and
identify one or more key patterns of the one or more patterns in an instance in which the importance level of a pattern of the one or more patterns exceeds a threshold defined by a domain model.

16. An apparatus according to claim 15, wherein the at least one memory including the computer program code is further configured to, with the at least one processor, cause the apparatus to:
determine a time period to be represented by the graphical output, wherein the time period is configured such that at least a portion of the one or more key patterns occur within the time period.

17. An apparatus according to claim 15, wherein the at least one memory including the computer program code is further configured to, with the at least one processor, cause the apparatus to:
determine one or more patterns in one or more related data channels that corresponds to an occurrence of the one or more key patterns; and
determine one or more significant patterns of the one or more patterns, wherein a significant pattern is a pattern that represents an anomaly.

18. An apparatus according to claim 14, wherein context information provides at least background or circumstance information having influenced the one or more key patterns in the primary data channel or the one or more significant patterns in the one or more related data channels.

19. An apparatus according to claim 14, wherein additional information related to the natural language annotation is displayed in the user interface in response to a user interaction with the user interface.

20. A computer program product comprising:
at least one computer readable non-transitory memory medium having program code instructions stored thereon, the program code instructions which when executed by an apparatus causes the apparatus at least to:
detect one or more patterns in a data channel derived from raw input data;
identify one or more patterns in another data channel also derived from the raw input data;
determine from one or more contextual channels context information for at least one of the one or more patterns in the data channel or the one or more patterns in the another data channel;
generate, using a natural language generation system that is configured to execute on a processor, one or more phrases describing the one or more patterns in the data channel and the one or more patterns in the another data channel, the one or more phrases generated by:
generating at least one message when a pattern from the one or more patterns in the data channel or a pattern from the one or more patterns in the another data channel satisfies one or more message requirements,
selecting one or more words to express a concept or a relation in the at least one message, and
applying a grammar to the selected one or more words; and
generate a graphical output, for display in a user interface, based on the data channel, the another data channel, the one or more contextual channels, and the one or more phrases, wherein the one or more phrases are interactively annotated on the graphical output of the data channel and the another data channel.

* * * * *